(12) United States Patent
Zhao

(10) Patent No.: US 7,221,444 B1
(45) Date of Patent: May 22, 2007

(54) METHOD AND SYSTEM FOR IMPROVED DEFECT SENSITIVITY FOR INSPECTING SURFACES

(75) Inventor: Guoheng Zhao, Milpitas, CA (US)

(73) Assignee: 3i Systems Inc., Sunnyvale, CA (US)

(*) Notice: Subject to any disclaimer, the term of this patent is extended or adjusted under 35 U.S.C. 154(b) by 0 days.

(21) Appl. No.: 11/251,129

(22) Filed: Oct. 14, 2005

(51) Int. Cl.
*G01N 21/00* (2006.01)

(52) U.S. Cl. .............................. 356/237.1; 356/237.4

(58) Field of Classification Search .. 356/237.1–237.5, 356/239.1–239.4, 394
See application file for complete search history.

(56) References Cited

U.S. PATENT DOCUMENTS 6,411,377 B1* 6/2002 Noguchi et al. ......... 356/237.4

2005/0110988 A1* 5/2005 Nishiyama et al. ...... 356/237.5

* cited by examiner

*Primary Examiner*—Hoa Q. Pham
(74) *Attorney, Agent, or Firm*—Joe Zheng

(57) ABSTRACT

Techniques for inspecting a substrate with improved defect sensitivity are disclosed. High sensitivity is achieved by reducing the noise due by using multiple laser beams for illumination, in which each beam is nearly collimated and illuminates uniformly a field of view. The images generated respectively by the laser beams are added incoherently by means of delivering the illumination beams incoherently in either time domain or space domain. According to one embodiment, all the illumination beams may not be interact with each other coherently so that the images generated by each laser beams can be summed together incoherently to average out possible excessive noise.

30 Claims, 8 Drawing Sheets

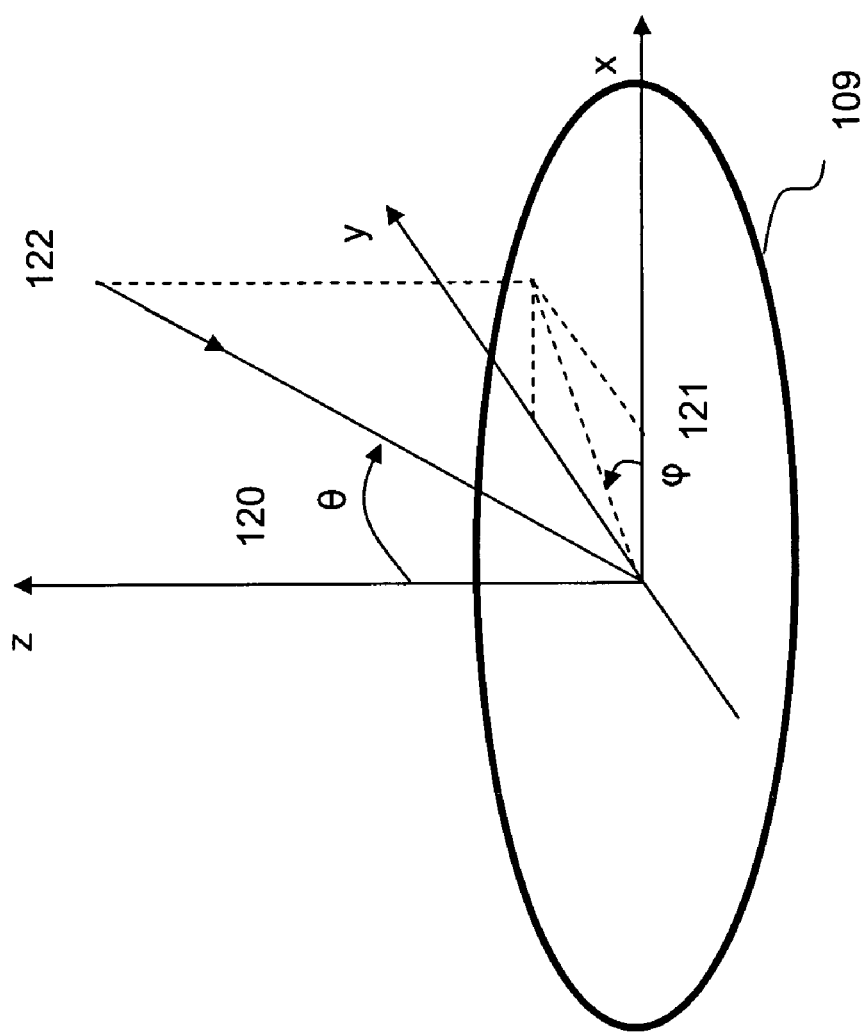

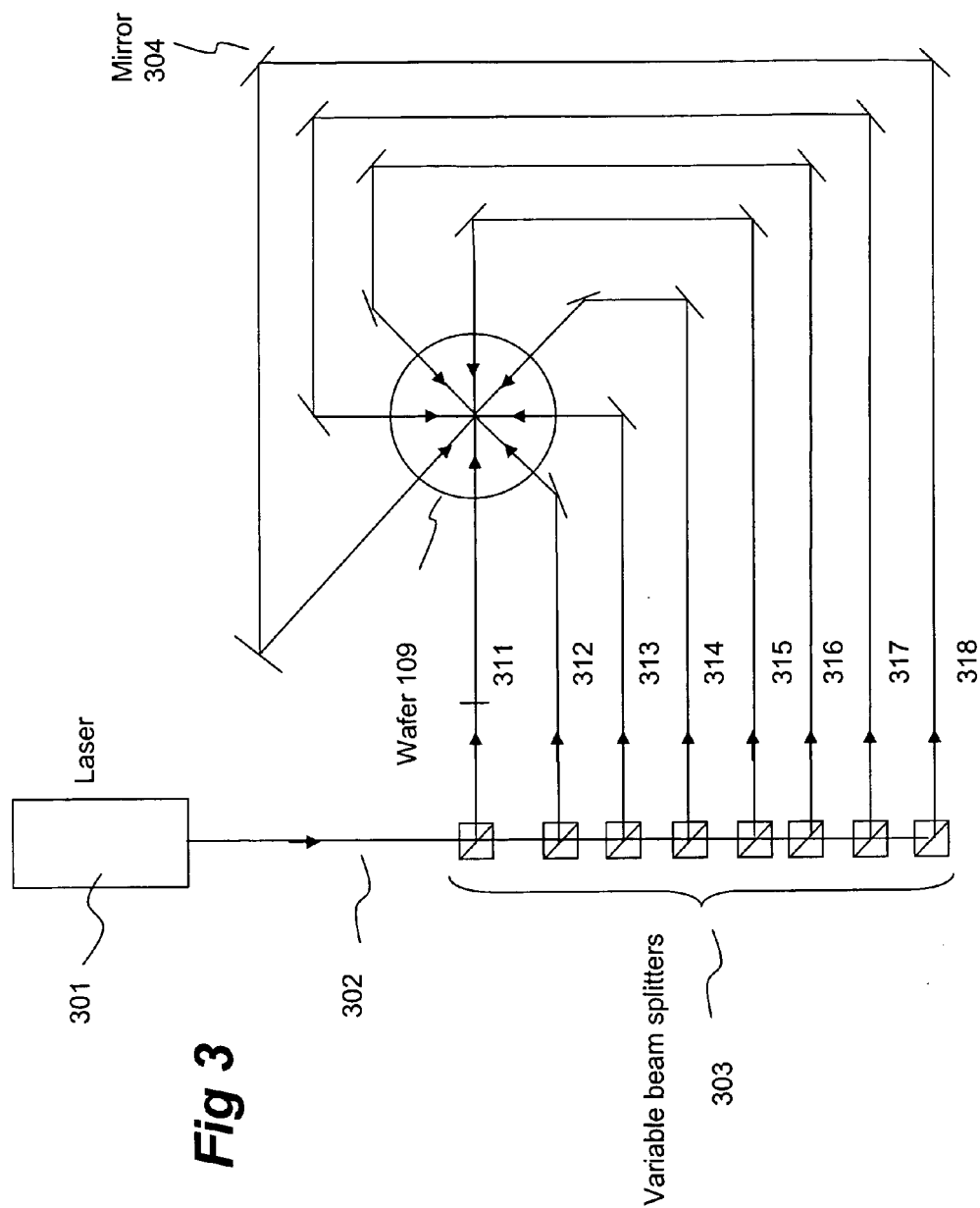

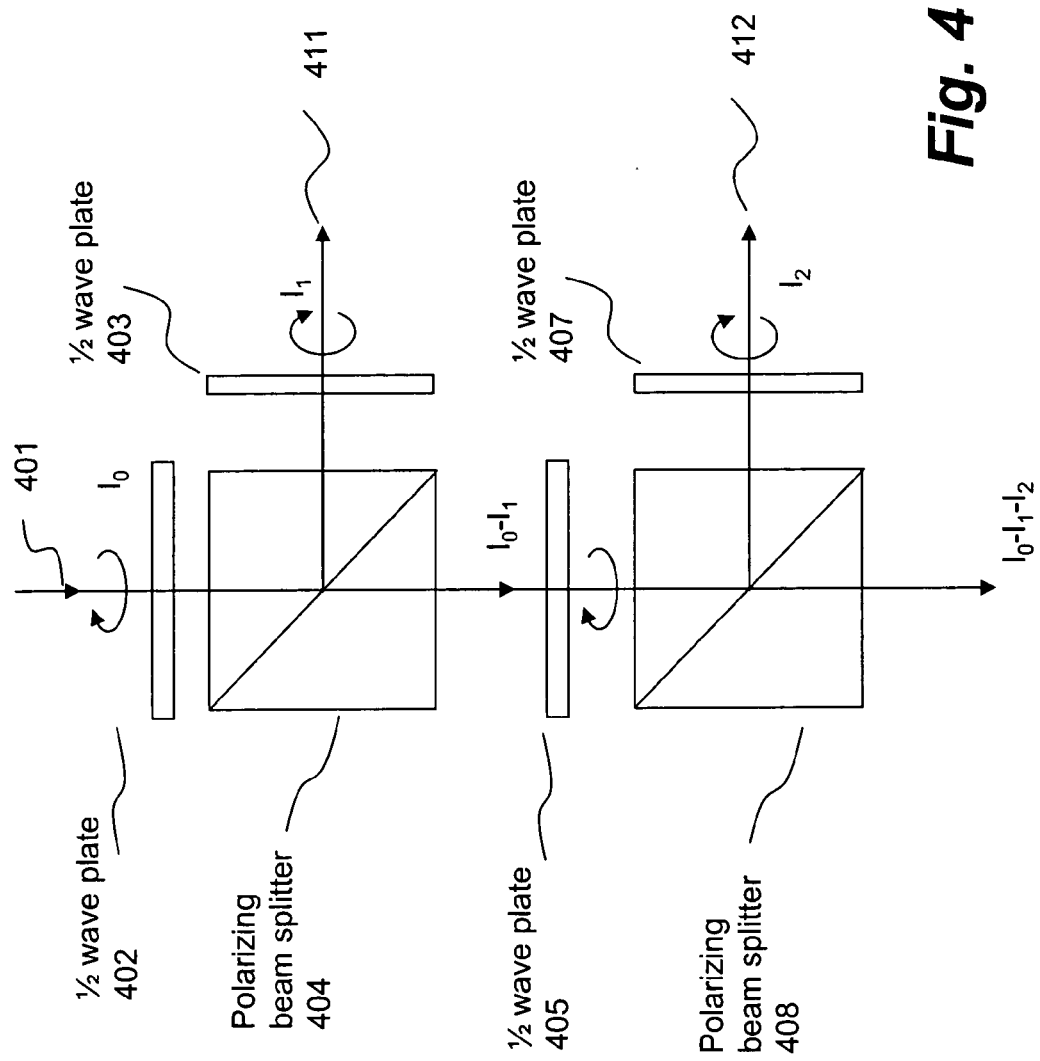

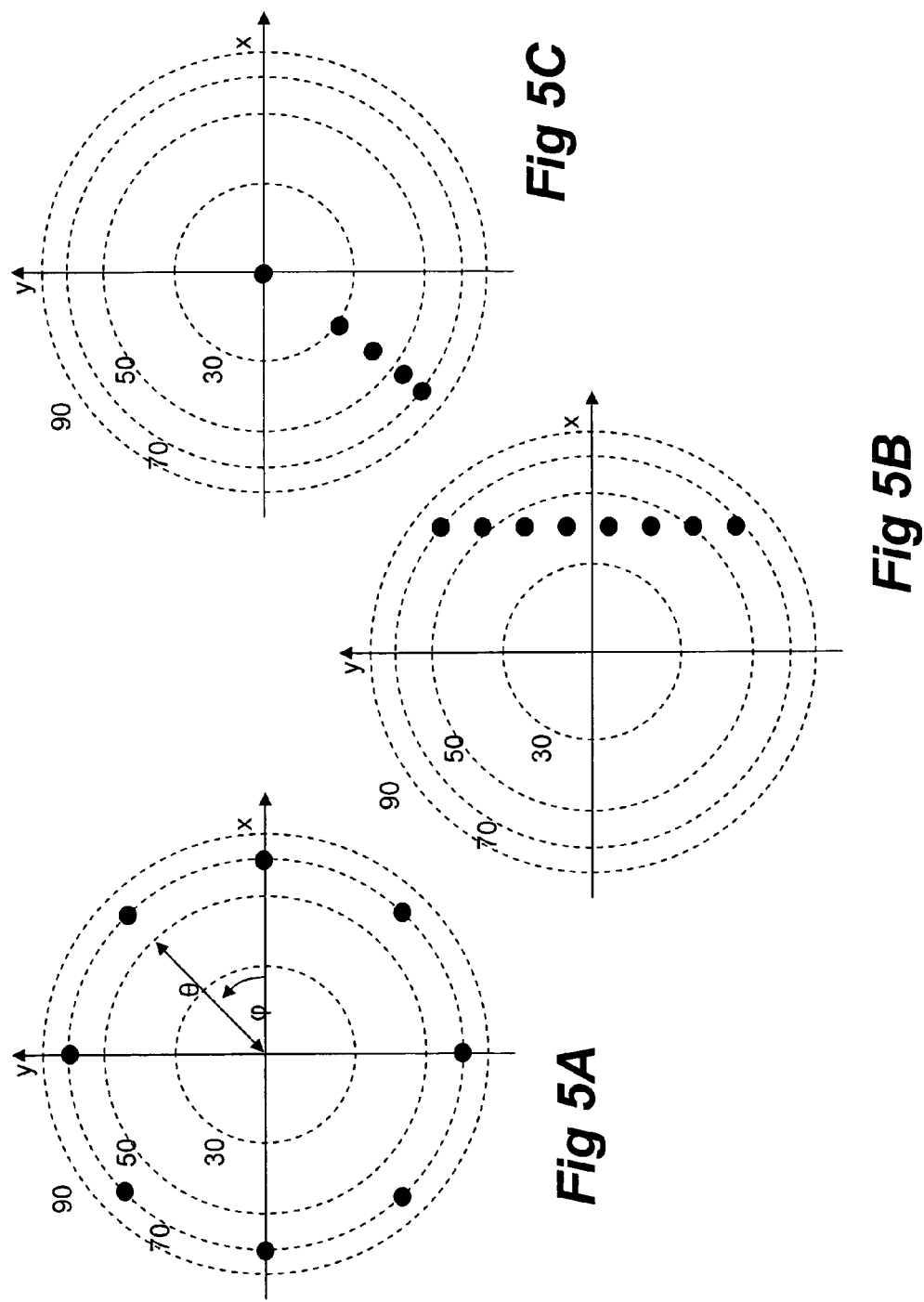

METHOD AND SYSTEM FOR IMPROVED DEFECT SENSITIVITY FOR INSPECTING SURFACES

BACKGROUND OF THE INVENTION

1. Field of the Invention

The invention is related in general to the area of inspection systems. In particular, the present invention is related to method and systems for detecting defects the dimensions of which may exceed the optical resolution limits of a given imaging system. The present invention may be advantageously used in fabrication processes for devices such as flat panel displays, lithography masks, and semiconductor wafers.

2. The Background of Related Art

Driven by the demand for performance enhancement and cost reduction, the design rule (DR) of integrated circuits (IC) shrinks every year as the technology of manufacturing IC progresses. In the current manufacturing process of IC volume production, pattern represent designs are imprinted on silicon wafers using optical lithography techniques. The minimum dimension of a pattern that can be imprinted may be well below the theoretical optical resolution limit. Various resolution enhancement technologies implemented in the lithography optics, mask designs, and resist engineering have overcome the optical resolution limit. However, the dimensions of various defects that may occur during the manufacturing process become smaller and smaller as the DR shrinks. The smallest defects, but critical to the performance of finished IC chips, that need to be detected and identified during the manufacturing process are only a fraction of the DR. The rapid progress in IC manufacturing technology has generated very demanding requirements on optical defect inspection.

The ability of optical inspection to detect the smallest defect is largely determined by a signal-to-noise ratio of the defect. The signal of a defect is to the first order determined by the optical resolution of an inspection tool, and to the second order by a number of parameters of the optics configuration, such as wavelength, the geometry of illumination and collection, polarization, and the modes of imaging. While the signal of a defect increases with the higher optical resolution, there are both theoretical and practical limits of the highest optical resolution that can be used in an optical inspection tool. As the limits of optical resolution are approached, other means of improving defect detection sensitivity have to be implemented and become critical in meeting the requirements of defect inspection in production line.

Two of the commonly used imaging modes in the conventional microscopy, bright field and dark field, have been applied to defect inspection in IC manufacturing process. Bright field imaging has the advantages of higher optical resolution since it can use the maximum numerical aperture (NA) of the imaging lens. However, the bright background of the optical image tends to reduce the dynamic range and results in higher background noise. On the other hand, dark field imaging has the advantages of reducing or eliminating the background, therefore highlighting defects. Although a portion of the NA space is used for the illumination in dark field, which results in a smaller usable NA for imaging, therefore lower optical resolution, an enhancement of the signal-to-noise of defect due to the reduction of background often makes up more than enough the loss of optical resolution. In addition, less amount of data to be acquired and processed at lower resolution often leads to a higher inspection speed and lower system cost. Nevertheless, one of the disadvantages of dark field imaging is that it generally requires high brightness light source for illumination, since the scattered light collected in dark field imaging is only a small fraction of the incident light.

Light sources used for defect inspection imaging include both broad band lamps and lasers. Lamps have lower brightness and are often inadequate in providing enough light intensity for dark field defect inspection, especially at high resolution where imaging pixel is small and number of photons per pixel is lower. Lasers have the highest brightness among various light sources, and their wide applications have helped the development of commercially available lasers that can generate intense light at various wavelengths, from infrared to deep ultra-violet (UV). Lasers are not only used for dark field inspections, but also for bright field inspection when lamps do not have enough brightness at a desired wavelength, especially in the deep UV range. These types of inspection technologies are disclosed in U.S. Pat. No. 6,943,876, U.S. Pat. No. 6,693,664, and U.S. Pat. No. 6,288,780.

Conventional dark field inspection uses an expanded beam to illuminate a field of view, the NA of the illumination beam is much smaller than the NA of the imaging lens. In most cases, it is close to zero when the laser beam is nearly collimated. There is a significant disadvantage of using nearly collimated laser beam for illumination, it tends to cause excessive noise in imaging a surface that is not perfectly smooth. In most of the intended applications of defect inspection, a substrate is coated with a thin film that is inherently rough on surface, or patterned with multiple layers of structures of the integrated circuits. When the NA of the illumination beam is very small, or the nearly collimated, the wave front of the illumination beam over the entire optical field of view is substantially coherent. As a result, the interference between neighboring scatters on the substrate amplifies any small variations of the pattern on substrate which increases the noise floor and degrades defect detection sensitivity.

An example of such noise is the speckle generated from a diffusive surface when illuminated by a laser. For defect inspection during IC manufacturing process, the excessive noise can be significant. Some of the materials used in IC manufacturing are inherently grainy, and the surface is rough when coated a thin film on wafer surface (e.g., poly silicon and metal). In addition, the process of generating an IC pattern on wafer has some small random variation while the dimension of the pattern printed on wafer may also have small variation. Defects are identified by comparing identical features printed on wafer, such as two identical dies or cells in memory device. The small variation is often the limiting noise in detecting defect. In the case of coherent imaging system, the small variation is amplified through the interference effect and reflected as excessive noise in the die to die or cell to cell comparison process.

Suppressing noise can improve defect detection sensitivity as effectively as enhancing defect signal, especially when the optical system operates near its theoretical limits. There is thus a great need for techniques to provide an effective way of reducing the excessive noise in imaging.

SUMMARY OF THE INVENTION

This section is for the purpose of summarizing some aspects of the present invention and to briefly introduce some preferred embodiments. Simplifications or omissions in this section as well as in the abstract and the title may be made to avoid obscuring the purpose of this section, the abstract and the title. Such simplifications or omissions are not intended to limit the scope of the present invention.

Broadly speaking, the present invention pertains to method and systems for detecting defects the dimensions of which may exceed the optical resolution limits of a given imaging system. An inspection system contemplated in accordance with the present invention may be advantageously used in fabrication processes for devices such as flat panel displays, lithography masks, and semiconductor wafers. According to one aspect of the present invention, multiple laser beams are employed to illuminate the same area on a moving substrate (e.g., silicon wafer). These laser beams are configured onto the surface of the substrate incoherently. The illuminated area is imaged by an imaging system including a sensor and one or more high resolution optical lenses. To minimize noises in images, the sensor is configured to integrate incoherently respective images generated by respective illuminating beams.

According to another aspect of the present invention, a laser beam is divided into a number of beams, each of the beams is expanded and shaped to a proper size so that a full optical field of view of the imaging lens is fully illuminated. The incident angle (polar angle) of the beams can be configured at substantially similar angles (e.g., 65 degrees). The incident planes (defined by the incident beam and the normal to the wafer surface) of the beams can be distributed uniformly over the 360 degree azimuth angle.

According to still another aspect of the present invention, a number of methods of reducing or eliminating the coherence among the multiple means are proposed. When the multiple laser beams are incoherent to each other, noise can be reduced by averaging effect of adding together incoherently all the images generated by each laser beam. However, in real applications, the multiple laser beams are preferably derived from a single laser source to reduce the cost and dimension of the entire system. Such multiple laser beams are coherent to each other. In one embodiment, a time delay integration (TDI) charge coupled device (CCD) sensor is used as the imaging detector. The unique property of TDI is used to eliminate the coherence among multiple laser beams. In another embodiment, a fiber bundle is used to deliver multiple laser beams through a conventional device to destroy the coherence (e.g., rotating or diffusing). The fiber bundle is then split into multiple bundles to deliver the multiple beams. In still another embodiment, a multi longitudinal mode laser, such as diode pumped solid state (DPSS) lasers operating at either visible or UV wavelength is used. Multi longitudinal mode lasers have short coherent length that may be on the order of a few millimeters. In this case, the multiple laser beams may be delayed in time domain by a distance that is longer than the coherent length, therefore become incoherent to each other when they arrive at the substrate surface. In addition, a pulsed laser can also be used in substantially similar manner, for example, a mode locking DPSS laser can generate laser pulses with duration of around 10 picoseconds (ps). Since light travels a distance of 3 mm in air within 10 ps, therefore a 20 mm delay between two laser beams can eliminate the coherence between the laser beams, and the total accumulated delay length for 8 beams is 160 mm.

According to yet another aspect of the present invention, various designs are provided to reduce coherent noise. The coherent noise is generally caused by the large extending of the tails in the optical point spread function. The optical image of an infinite small point has a strong main lobe. However, the point spread function of an actual imaging system has a main lobe and decaying oscillating side lobes which are the source of excessive noise due the interference between neighboring scatters. A circularly symmetric optical plate with a transmission profile of gradually decreasing from center to edge is placed at the Fourier plane of the imaging lens, thus reducing the amplitude of the side lobes of the PSF dramatically, which in return reduces the noise due to coherent imaging.

The present invention may be implemented as a method, an apparatus or a part of system. According to one embodiment, the present invention is a method for detecting defects, the method comprises: providing a plurality of laser beams to illuminate a substrate on a moving mechanism, each of the laser beams directed by one or more reflectors to illuminate an elongated area of a field of view of a lens positioned to focus on a surface of the substrate being moved across, wherein a distance between any two of the laser beams is greater than a width of one of the laser beams; generating images sequentially as the substrate moves across the lens, each of the images corresponding to one of the laser beams; and integrating the images to minimize possible noise in each of the images to produce a final image.

According to one embodiment, the present invention is an apparatus for detecting defects, the apparatus comprises: an imaging system including at least a lens and a photo detector; a mechanism moving a substrate under the imaging system; a plurality of reflectors producing multiple laser beams, each of the beams illuminating an elongated area of a field of view of the lens positioned to focus on a surface of the substrate being moved across, wherein a distance between any two of the laser beams is greater than a width of one of the laser beams. The photo detector generates images sequentially as the substrate moves across the lens, each of the images corresponding to one of the laser beams, the images are then integrated to minimize possible noise in each of the images to produce a final image.

One of the objects, features, advantages, benefits of the present invention is to provide method and systems for detecting defects the dimensions of which may exceed the optical resolution limits of a given imaging system.

Other objects, features, advantages, benefits of the invention will become more apparent from the following detailed description of a preferred embodiment, which proceeds with reference to the accompanying drawings

BRIEF DESCRIPTION OF THE DRAWINGS

These and other features, aspects, and advantages of the present invention will become better understood with regard to the following description, appended claims, and accompanying drawings where:

FIG. 1C shows an incident angle of one of the illuminating beams defined by a polar angle and an azimuth angle;

FIG. 3 is a functional diagram showing the splitting and delaying of multiple laser beams for illumination when the laser has a short coherent length;

FIG. 4 illustrates that the intensity and polarization of each illumination beam can be independently controlled through a combination of half wave plate and polarizing beam splitter; and FIG. 5A, FIG. 5B, and FIG. 5C shows, respectively, three exemplary placements or distribution of the multiple laser beams.

DETAILED DESCRIPTION OF THE PREFERRED EMBODIMENT

The present invention pertains to designs of detecting defects the dimensions of which may exceed the optical resolution limits of a given imaging system. An inspection system contemplated in accordance with the present invention may be advantageously used in fabrication processes to detect defects in various types of substrates. With carefully arranged multiple laser beams as the illumination sources, images from the respective beams are integrated in a photo detector and subsequently analyzed. Defects, even exceeding the optical resolution limits, can be detected.

The detailed description of the present invention is presented largely in terms of procedures, steps, logic blocks, processing, or other symbolic representations that directly or indirectly resemble the operations of devices or systems contemplated in the present invention. These descriptions and representations are typically used by those skilled in the art to most effectively convey the substance of their work to others skilled in the art.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments.

Figure 1A:
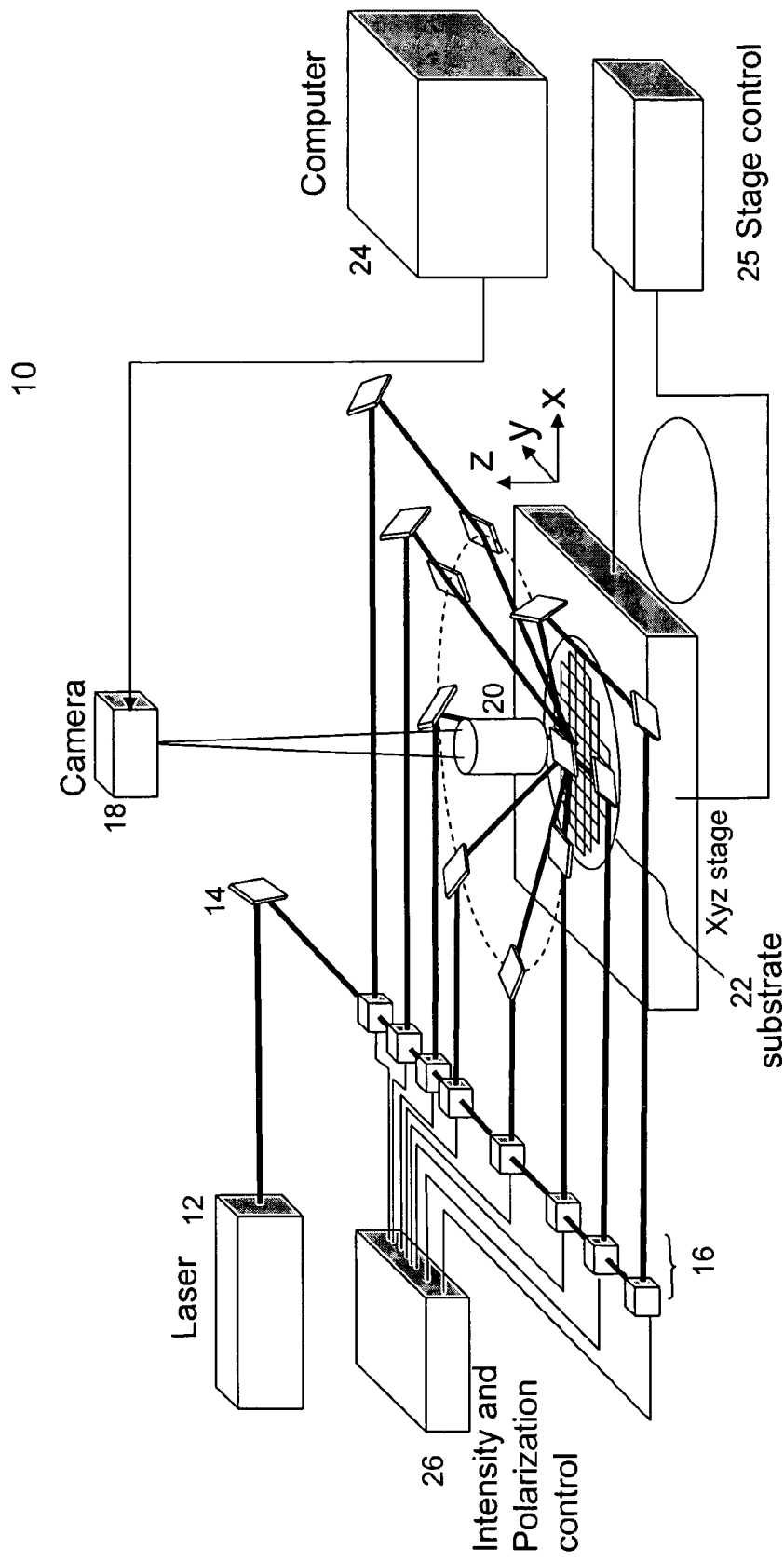
FIG. 1A shows an exemplary configuration according to one embodiment of the present invention.

Referring now to the drawings, in which like numerals refer to like parts throughout the several views. FIG. 1A shows an exemplary configuration 10 according to one embodiment of the present invention. The configuration 10 includes a laser source 12 producing a light beam projected onto a mirror 14. The mirror 14 transmits the light beam to an array of variable beam splitters 16 that subsequently produces multiple beams. The intensity and polarization of each beam are independently controlled by a control unit 26. In general, the beams are coherent with each other when they are derived from a single source, and may cause interference fringes when they overlap with each other. The interference fringe is not desirable in this application since it destroys the uniformity of illumination and becomes the source of coherent noise. As described below, such coherency among the beams has been successfully overcome according one aspect of the present invention.

The configuration 10 further includes a photo detector 18 coupled to a lens 20. As a substrate 22 moves across a field of view of the lens 20, a sequence of images are respectively produced by the photo detector 18 that transports the images to a computing device 24. In general, the images from the photo detector 18 are analog and shall be digitalized (e.g., in an A/D converter or a data translation board) before processing in the computing device 24. The computing device 24 is loaded one or more applications to process the acquired images to detect the defects on the substrate 22. The stage control 25 is provided to control the movement of the substrate 22 and configured to synchronize with or be synchronized with the operation of the photo detector 18 or/and the computing device 24.

Figure 1B:
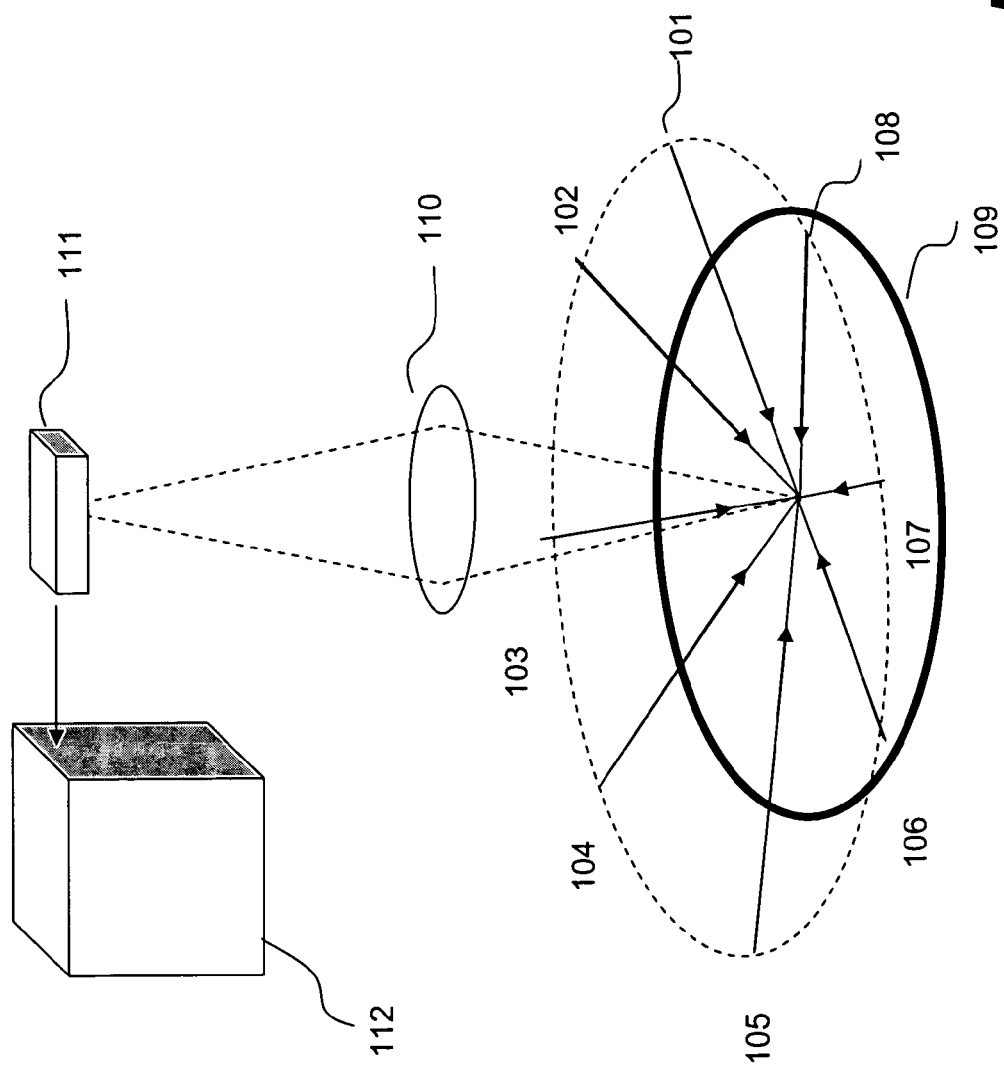
FIG. 1B shows a zoomed portion of FIG. 1A that uses multiple collimated laser beams for illuminating a field of view of an imaging lens.

Referring now to FIG. 1B, there shows a zoomed portion of FIG. 1A that uses multiple collimated laser beams for illuminating a field of view of an imaging lens 110. The beams 101–108 are respectively calibrated to illuminate concurrently the optical field of view of the imaging lens 110 while the substrate 109 is moving (e.g., over a convey belt or by a mechanical xy stage). An image is formed by the imaging lens 110 onto a photo detector 111. Depending on implementation, the photo detector may be a 2-D image sensor or an image scanner. According to one embodiment, the photo detector 111 is a time delay integration (TDI) line scan sensor provided by DALSA Corporation (http://www-.dalsa.com). Preferably, the moving speed of the substrate 109 is synchronized with the line scanning rate of the camera 114 to generate a sequence of images of the substrate 109. The acquired images are sequentially sent to a computing device 112 for processing.

For simplicity, FIG. 1A or FIG. 1B shows only eight illuminating beams. It should be noted that the exact number of the illuminating beams may be determined accordingly in an application. According to one aspect of the present invention, the number of the illuminating beams is greater than two. In other words, multiple illuminating beams are used to illuminate a field of view of the lens 20 or a predefined area through which a substrate is moving through.

The incident angles of the illumination beams 101–108 are substantially different, and preferably uniformly in circularly symmetric distribution around an axis that is normal to the surface of the substrate 109. In one embodiment, the axis is the optical axis of the imaging lens 110. An incident angle of one of the illuminating beams is defined by a polar angle 120 and an azimuth angle 121, as shown in FIG. 1C. The xyz Cartesian coordinates are so defined that the surface of the substrate 109 is right in the xy plane, and a surface normal thereof is along the z axis.

In one embodiment, the incident angles of the 8 beams shown in FIG. 1A or FIG. 1B are given in the following table:

| Beam number | Polar angle (degree) | Azimuth angle (degree) |
|---|---|---|
| 101 | 70 | 0 |
| 102 | 70 | 45 |
| 103 | 70 | 90 |
| 104 | 70 | 135 |
| 105 | 70 | 180 |
| 106 | 70 | 225 |
| 107 | 70 | 270 |
| 108 | 70 | 315 |

Figure 1D:
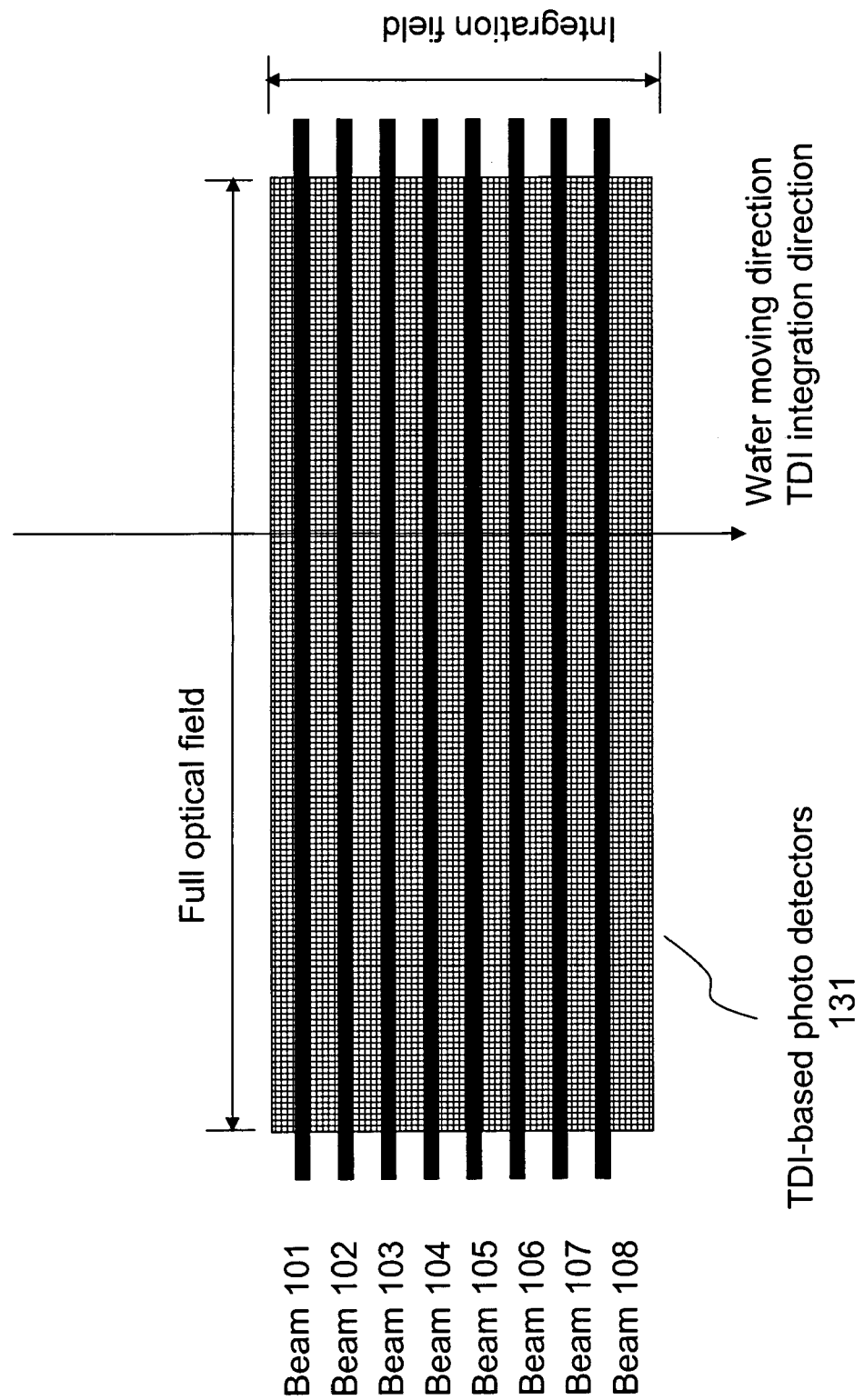
FIG. 1D shows the positioning of each laser beam within an optical field of view.

FIG. 1D shows the positioning of each laser beam within an optical field of view. A photo detector 131 acquires an image of a moving object (e.g., a substrate) by synchronously shifting photon electrons of the entire line (horizontal) of pixels along the moving direction (vertical) of the moving object. During the vertical shifting, the photon electrons are accumulated over the entire integration field. Each line of pixels is read out at the end of the vertical shift to form an aerial image of the moving object. The time delay integration in the vertical direction is designed to enhance the sensitivity of a line scanner by allowing a longer time of exposure so to collect more photons than a conventional line scanner does. One of the aspects in the present inventions is to use the unique properties of the TDI scanner to eliminate the illumination coherence of the multiple laser beams.

In one embodiment, the projection on a substrate by each laser beam is shaped into an elongated stripe (e.g., a narrowly long rectangular beam) with the longer dimension parallel to the TDI line scan direction (e.g., horizontal direction as shown in FIG. 1D). The multiple laser beams are separated by a distance that is greater than the width of a beam and distributed preferably uniformly in the TDI integration direction (e.g., vertical direction as shown in FIG. 1D). Because of the spatial separation of the multiple laser beams, there is no interference between the beams. In the normal mode of operation of a TDI scanner, the photo electrons generated by each individual beam are accumulated. Images generated by each illuminating beam, which is coherent imaging by itself, are summed, wherein the multiple laser beams are added together incoherently. The averaging of the multiple individual coherent images is done in real time before the images are quantized and digitized, therefore reducing the excessive noise due to coherent imaging, without any delay of image acquisition and processing.

Figure 2:
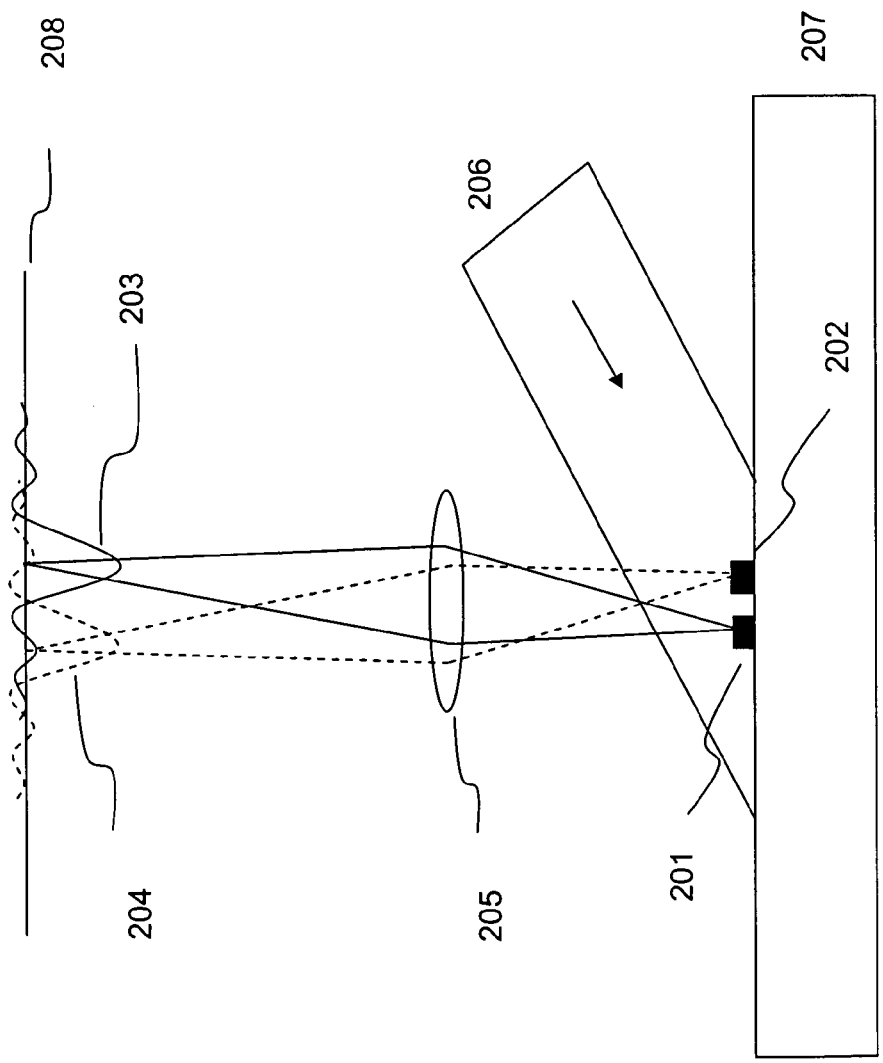
FIG. 2 provides an illustration of the cause of excessive noise in dark field imaging when illumination is a single nearly collimated laser beam.

Referring now to FIG. 2, there provides an illustration of the cause of excessive noise in dark field imaging when illumination is a single nearly collimated laser beam. When two neighboring pattern features 201 and 202 are illuminated by a collimated laser beam 206, the scattered light caused by the two neighboring pattern features 201 and 202 are collected by the imaging lens 205 and brought into focus onto the image plane 208. For features smaller than a given optical resolution, the image of the feature is close to the point spread function (PSF) of the imaging lens. When two features are separated by a distance similar to the size of the optical PSF, the overlapping part of the PSF-like images 203 and 204 of the two features adds coherently as shown in FIG. 2.

The manufacturing process of IC is a complicated configuration involving a number of processes and materials. As the DR shrinks, it becomes increasingly difficult to control the manufacturing process, therefore the small variations of the pattern features become increasingly more critical noise source for defect inspection.

The theory of image formation of coherent and incoherent optical system based on linear system and Fourier transform can be found in "Principal of Optics", M. Born and E. Wolf, which is hereby incorporated by reference. Based on the same principal, the amplification of noise and the reduction of noise through averaging are explained in a simplified manner as follows.

Again referring to FIG. 1C, the phase distribution at the substrate surface of a plane wave incident on the substrate at an incident angle ($\theta$, $\phi$) is given by:

$$W = \frac{2\pi}{\lambda}(x\sin\theta\cos\phi + y\sin\theta\sin\phi) \quad (1)$$

where $\lambda$ is the wavelength and (x,y) are the spatial coordinates on the substrate surface. Now considering two scatters on the surface, without losing generality, the two position coordinates of the two scatters can be chosen to be at (0,0) and (d,0). The phase difference between the two scatters due to illumination is then given by:

$$W = \frac{2\pi}{\lambda}d\sin\theta\cos\phi \quad (2)$$

The electric field at the image plane is given by the coherent addition of the two amplitude PSFs from the two scatters formed by the imaging lens. It is assumed that the two scatters are much smaller than the wavelength $\lambda$ and can be treated mathematically as delta functions. The amplitude distribution at the image plane is thus given by:

$$E = [A\delta(x) + e^{iW}B\delta(x-d)] \otimes J(x) = AJ(x) + e^{iW}BJ(x-d) \quad (3)$$

where $J(x)$ is the point spread function of the imaging lens, for an aberration free imaging lens with circular uniform aperture, it is given by:

$$J(x) = \frac{\lambda}{\pi NA} \frac{J_1\left(\frac{2\pi NA}{\lambda}x\right)}{x} \quad (4)$$

where $J_1(x)$ is the Bessel function of the first kind. $A_1$ and $A_2$ are the complex amplitude of the two scatters respectively. The intensity of the image is given by:

$$I = |E|^2 = |A|^2 J(x)^2 + |B|^2 J(x-d)^2 + 2|A||B||J(x)||J(x-d)|\cos(W+\Delta) \quad (5)$$

where $\Delta$ is the phase difference between two complex amplitudes of the scatters that is induced by the scattering process. The first two terms are the result of an ideal incoherent imaging system. The third term is the interference term between the two scatters, which is generally the source of excessive noise due to coherent imaging.

A small variation, for example, of the phase change which can be a result of any of the changes due to pattern shape, size, or material properties becomes the noise in the image and is given by the following equation:

$$\delta I \propto \sin(W+\Delta)(\delta\Delta) \quad (6)$$

One of the features in the present invention is that the excessive noise can be reduced by using multiple illumination beams. In a simplified example in which both the scatters and substrate are isotropic, the scattered electric field is independent of the azimuth angle of the incident beam. For N incident beams that are incoherent to each other, the image intensity is given by:

$$I = \sum_{m=1}^{N} a_m |E|_m^2 \quad (7)$$

where $a_m$ is the intensity of the m th beam. The noise of equation (6) due to the third term of equation (4) becomes:

$$\delta I \propto \sum_{m=1}^{N} \sin(W_m + \Delta)(\delta\Delta) \quad (8)$$

and $$W_m = \frac{2\pi}{\lambda} d\sin\theta\cos\phi_m \qquad (9)$$

The noise may be reduced to zero if the phase term $W_m$ are in pairs of reversed phase, but only for two scatters at a specific distance apart because $W_m$ is also dependent on the distance d between two points, as shown in equation (9). In addition, the scatters are generally distributed in all directions, therefore the N illumination beams preferably spread uniformly over the full range of 0 to 360 degrees to achieve the maximum averaging effect.

Equation (9) also indicates that the averaging effect becomes less effective when the polar angles of the incident beams are small. The extreme case is that when the polar angle θ is close to zero, thus the phase distribution of illumination beam on substrate becomes less dependent on the azimuth angle. In other words, even though the beams are incoherent with each other, but the coherent images generated by each beam becomes more correlated, and averaging becomes less effective. The same principal applies to the beams at large polar angle, but separated by a small azimuth angle.

As shown in equation (8), in order for the averaging to be effective, $W_m$ needs to be substantially different for different beams, or even in opposite signs. Although the random noise decreases with the number of averaging, due to the small phase difference between the beams separated by a small incident angle, or the strong correlation between the images generated by such illumination beams, there is an optimum number of illumination beams, or a range of the number of illumination beams that is a good balance between noise reduction and system complexity.

Lasers are available in many different modes of operations. The coherent length of a laser is determined by the spectral bandwidth, or the number of longitudinal modes. For example, a DPSS laser has a coherent length of a few millimeters when operating in multi-longitudinal modes. These types of lasers can be used for multi-beam illumination as well. According to one embodiment, FIG. 3 is a functional diagram showing the splitting and delaying of multiple laser beams for illumination when the laser has a short coherent length. According to one embodiment, the laser beam 302 from a laser source 301 is split by a set of variable beam splitters into multiple beams, there are eight beams shown in FIG. 3. A variable beam splitter may a combination of a half wave plate and a polarizing beam splitter, or a variable transmission to reflection thin film coating. Each beam is directed by different mirrors 304 to the surface of the substrate 109 to illuminate the optical field of view of the imaging lens. The beam splitters and mirrors are so arranged that the optical path length of each laser beam from the laser to the surface of the substrate 109 is different while the optical path length difference between any two laser beams is greater than the coherent length of the laser. For example, a multimode DPSS laser has a coherent length of 5 mm, the optical path length difference may be made to be greater than, for example, 30 mm. The delay length is compatible with typical dimensions of defect inspection tools, which are around 1000 mm.

The intensity and polarization of each illumination beam can be independently controlled through a combination of half wave plate and polarizing beam splitter, as shown in FIG. 4. For a linearly polarized laser beam 401, the first half wave plate 402 rotates the polarization to a desired angle so that the laser beam reflected by polarizing beam splitter 404 has the desired intensity. The intensity $I_1$ of beam 411 may be adjusted from 0 to 1 normalized to the intensity $I_0$ of laser beam 401. The polarization of beam 411 can be controlled by another half wave plate 403, to be either P-polarization, S polarization, or a linear polarization at any desired angle with respect to the incident plane of the illumination beam. Similarly, the intensity and polarization of the second beam 412, and other beams (not shown in the figure) can be adjusted to desired value.

According to another embodiment, the intensity and polarization of individual illumination beams are adjusted in groups as the illumination beams may be divided into groups. The printed patterns (e.g., dies) on a wafer are generally in rectangular shape. Further the patterns generally include either horizontal or vertical lines (e.g., layouts or conductors). When inspecting these types of patterns, the illumination beams may be divided into two groups, as shown in FIG. 3. The four illumination beams that have incident plane at 45 degree angle with respect to either the horizontal lines or the vertical lines are grouped into one group while the illumination beams having the incident planes either parallel or perpendicular to the pattern lines are grouped into another group. It may be appreciated that only the intensity ratio between the two groups needs to be adjustable, therefore the setting of the inspection configuration can be considerably simplified.

According to one embodiment, pulse lasers are used. For example, a mode locking DPSS laser has a pulse width of around 10 picoseconds (ps), during which time the laser pulse travels 3 mm in air. The delay between laser beams may be greater than 18 mm, so that the laser pulses arrives at a substrate surface at substantially different time, therefore separated in time domain. The total time delay is then N times 60 ps, for example, 480 ps for 8 beams. The separation in time is long enough for the laser pulses not to overlap, but still shorter than the integration time of a TDI-based camera, which may be on the order of microseconds, more than 1000 times the total delay time. In this case, the images generated by each laser beam are from substantially the same field of view, and added incoherently due to the separation in time domain.

Although a single laser source is preferred for simpler system and lower cost, multiple laser sources, each for a laser beams, can be used. In one embodiment, compact and low cost lasers (e.g., laser diodes) are used and packaged in multiple laser configurations. In this case, the laser beams are substantially incoherent to each other, the methods of separation in time or space domain is not necessary. In any case, the considerations for the above angular distribution of the incident beams still apply.

Many different arrangements of the incident angles of the multiple beam illumination are possible. The optimum illumination angles are largely determined by the geometry of the pattern and material properties of the pattern and substrate. For example, when the patterns on the substrate are circular symmetric, such as contact holes on a substrate, a circularly symmetric distribution of the illumination beams, as shown in FIG. 5A, is preferable and may produce better signal-to-noise ratio of a defect. On the other hand, if the patterns on a substrate are parallel lines, then the illumination beams arranged in a row, as shown in FIG. 5B, may produce better signal-to-noise ratio. For patterns in a thin transparent layer or multiple layers of patterns, such as metal lines underneath a transparent layer of dielectric materials, the illumination beams with substantial different polar angles, as shown in FIG. 5C may produce better signal-tonoise ratio of defects. The arrangement of illumination beams presented in the FIGS. 5A, 5B and 5C are given as examples, other arrangements that are optimized for a specific type of patterns on a substrate are possible and can be readily appreciated by those skilled in the art given the detailed description herein.

In addition, the incident angles may be variable, and the optimum angle (angles) may be determined by empirical testing with the specific sample of the patterns on the substrate. One test sample may be used to find out the optimum angles of illumination by maximizing the signal-to-noise ratio of the defects of interest on the substrate, and the angles and other parameter are saved in the computer that controls the system, and subsequent substrates are inspected with the saved configuration.

The present invention has been described in sufficient details with a certain degree of particularity. It is understood to those skilled in the art that the present disclosure of embodiments has been made by way of examples only and that numerous changes in the arrangement and combination of parts may be resorted without departing from the spirit and scope of the invention as claimed. Accordingly, the scope of the present invention is defined by the appended claims rather than the foregoing description of embodiments.

I claim:

1. A method for detecting defects, the method comprising:
providing a plurality of laser beams to illuminate a substrate on a moving mechanism, each of the laser beams directed by one or more reflectors to illuminate an elongated area of a field of view of a lens positioned to focus on a surface of the substrate being moved across the lens, wherein a distance between any two of the laser beams is greater than a width of one of the laser beams, the laser beams are sequentially delayed in time domain by the distance longer than a coherent length in the laser beams as such the laser beams become incoherent to each other when they eventually arrive at the substrate;
generating images sequentially as the substrate moves across the lens, each of the images corresponding to one of the laser beams;
integrating the images to minimize possible noise in each of the images to produce a final image.

2. The method as recited in claim 1, wherein dimensions of some of the defects exceed optical resolution limits of a given imaging system producing the images.

3. The method as recited in claim 2, wherein scattering signals as a result of two neighboring defects, after imaged, cause a phase difference due to illumination by the laser beams.

4. The method as recited in claim 3, wherein such a phase difference leads to an intensity change in the final image.

5. The method as recited in claim 1, wherein each of the laser beams is distributed uniformly in the elongated area.

6. The method as recited in claim 5, wherein none of the laser beams interact with each other coherently so that the images can be integrated incoherently to average out the possible noise.

7. The method as recited in claim 6, wherein incident angles of the laser beams are configured substantially similar.

8. The method as recited in claim 7, wherein the laser beams are respectively split from a single laser source using a corresponding number of variable beam splitters.

9. The method as recited in claim 8, wherein each of the laser beams is so manipulated that possible coherence among the laser beams is minimized.

10. The method as recited in claim 8, wherein the laser beams are divided into at least two groups, the laser beams in one group are manipulated differently from the laser beams in another group.

11. The method as recited in claim 1, wherein the laser beams are distributed uniformly around the field of view, along one side of the field of view or along a particular direction across the field of view.

12. The method as recited in claim 1, wherein the laser beams are distributed with specific incident angles or azimuth angles through empirical testing in accordance with specific patterns on the substrate to minimize possible noise in the images.

13. The method as recited in claim 1, wherein the laser beams are from a single laser by delaying the laser beams differently in time domain, where a delay is longer than a coherent length of the single laser.

14. The method as recited in claim 13, wherein the single laser is a continuous wave (CW) laser, a single longitudinal mode laser, a multi longitudinal mode laser, or a pulsed laser.

15. The method as recited in claim 13, wherein each of the laser beams is adjusted independently with respect to polarization or/and intensity thereof.

16. An apparatus for detecting defects, the apparatus comprising:
an imaging system including at least a lens and a photo detector;
a mechanism moving a substrate under the imaging system;
a plurality of reflectors producing multiple laser beams, each of the beams illuminating an elongated area of a field of view of the lens positioned to focus on a surface of the substrate being moved across the imaging system, wherein a distance between any two of the laser beams is greater than a width of one of the laser beams, the laser beams are sequentially delayed in time domain by the distance longer than a coherent length in the laser beams as such the laser beams become incoherent to each other when they eventually arrive at the substrate,
wherein the photo detector generates images sequentially as the substrate moves across the lens, each of the images corresponding to one of the laser beams, the images are then integrated to minimize possible noise in each of the images to produce a final image.

17. The apparatus as recited in claim 16, wherein dimensions of some of the defects exceed optical resolution limits of the imaging system.

18. The apparatus as recited in claim 17, wherein scattering signals as a result of two neighboring defects, after imaged, cause a phase difference due to illumination by the laser beams.

19. The apparatus as recited in claim 18, wherein such a phase difference leads to an intensity change in the final image.

20. The apparatus as recited in claim 16, wherein each of the laser beams illuminates uniformly in the elongated area.

21. The apparatus as recited in claim 20, wherein none of the laser beams interact with each other coherently so that the images can be integrated incoherently to average out the possible noise.

22. The apparatus as recited in claim 21, wherein incident angles of the laser beams are configured substantially similar.

23. The apparatus as recited in claim 22, wherein the laser beams are respectively split from a single laser source using a corresponding number of variable beam splitters.

24. The apparatus as recited in claim 23, wherein each of the laser beams is so manipulated that possible coherence among the laser beams is minimized.

25. The apparatus as recited in claim 24, wherein the laser beams are divided into at least two groups, the laser beams in one group are manipulated differently from the laser beams in another group.

26. The apparatus as recited in claim 16, wherein the laser beams are distributed uniformly around the field of view, along one side of the field of view or along a particular direction across the field of view.

27. The apparatus as recited in claim 16, wherein the laser beams are distributed with specific incident angles or azimuth angles through empirical testing in accordance with specific patterns on the substrate to minimize possible noise in the images.

28. The apparatus as recited in claim 16, wherein the laser beams are from a single laser by delaying the laser beams differently in time domain, where a delay is longer than a coherent length of the single laser.

29. The apparatus as recited in claim 28, wherein the single laser is a continuous wave (CW) laser, a single longitudinal mode laser, a multi longitudinal mode laser, or a pulsed laser.

30. The apparatus as recited in claim 28, wherein each of the laser beams is adjusted independently with respect to polarization or/and intensity thereof.

* * * * *